United States Patent [19]

Hirai et al.

[11] Patent Number: 5,639,915
[45] Date of Patent: Jun. 17, 1997

[54] PROCESS FOR THE PRODUCTION OF ANILINE DERIVATIVES

[75] Inventors: Kenji Hirai; Emiko Ejiri; Tomoyuki Yano; Kiyomi Aizawa, all of Kanagawa-ken, Japan

[73] Assignees: Sagami Chemical Research Center; Kaken Pharmaceutical Co., Ltd., both of Tokyo, Japan

[21] Appl. No.: 401,781

[22] PCT Filed: Sep. 10, 1993

[86] PCT No.: PCT/JP93/01296

§ 371 Date: Mar. 10, 1995

§ 102(e) Date: Mar. 10, 1995

[87] PCT Pub. No.: WO94/06753

PCT Pub. Date: Mar. 31, 1994

[30] Foreign Application Priority Data

Sep. 11, 1992 [JP] Japan ..................... 4-267804

[51] Int. Cl.⁶ .................. C07C 213/00; C07C 213/06
[52] U.S. Cl. .................. 564/442; 564/393; 564/443
[58] Field of Search .......................... 564/442

[56] References Cited

U.S. PATENT DOCUMENTS

| | | | |
|---|---|---|---|
| 4,484,941 | 11/1984 | Nagano et al. | 564/442 X |
| 4,818,272 | 4/1989 | Hirai et al. | 548/226 X |
| 5,118,849 | 6/1992 | Schallner et al. | 564/442 |

FOREIGN PATENT DOCUMENTS

| | | |
|---|---|---|
| 0 150 064 | 7/1985 | European Pat. Off. |
| WO94/06753 | 3/1994 | WIPO |

*Primary Examiner*—Richard L. Raymond
*Attorney, Agent, or Firm*—Nixon & Vanderhye P.C.

[57] ABSTRACT

Industrial process for the efficient production of aniline derivatives which are important intermediates for the manufacture of oxazolidinedione derivatives and tetrahydrophthalimide derivatives which are useful as active ingredients of herbicides. The process starts from 2,4-dihalo-5-aminophenol or bis(2,4-dihalo-5-aminophenyl)carbonate and selectively cycloalkylates or alkynylates the hydroxy group without protecting the amino group, whereby aniline derivatives having the cycloalkyloxy group or alkynyloxy group can be produced in high yield.

3 Claims, No Drawings

PROCESS FOR THE PRODUCTION OF ANILINE DERIVATIVES

CROSS-REFERENCE TO RELATED APPLICATIONS

This application is a 371 of PCT/JP93/01296 filed 10 Sep. 1993.

TECHNICAL FIELD

This invention relates to a process for producing an aniline derivative of the general formula (3):

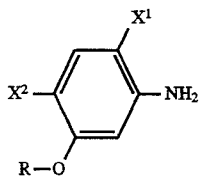

(where $X^1$ and $X^2$ represent a halogen atom and R represents an optionally substituted cycloalkyl group having 3–12 carbon atoms or an optionally substituted alkynyl group having 3–6 carbon atoms) by reacting a halogen-substituted aminophenol derivative of the general formula (1):

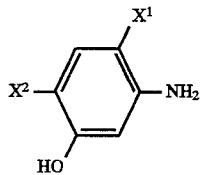

with an alkylating agent of the general formula (2):

R—Y    (2)

either in a two-layer system consisting of an aqueous solution of an alkali metal hydroxide and an organic solvent in the presence of a phase transfer catalyst or in an organic solvent in the presence of an alkali metal carbonate.

The invention also relates to a process for producing an aniline derivative of the general formula (3):

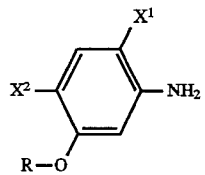

(where $X^1$ and $X^2$ represent a halogen atom and R represents an optionally substituted cycloalkyl group having 3–12 carbon atoms or an optionally substituted alkynyl group having 3–6 carbon atoms) by reacting a bis(amino-substituted phenyl)carbonate derivative of the general formula (4):

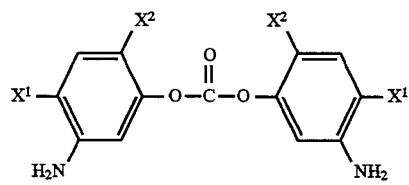

with an alkylating agent of the general formula (2):

R—Y    (2)

either in a two-layer system consisting of an aqueous solution of an alkali metal hydroxide and an organic solvent in the presence of a phase transfer catalyst.

More specifically, this invention relates to processes for the production of intermediates for the manufacture of oxazolidinedione and tetrahydrophthalimide, as well as tetrahydroindazole derivatives which are useful as active ingredients of herbicides as described in Japanese Patent Public Disclosure No. Sho. 62-167713 or Japanese Patent Public Disclosure Nos. Hei. 4-145071 and Hei. 4-164067.

BACKGROUND ART

The production of aniline derivatives of the general formula (3) from halogen-substituted aminophenol derivatives of the general formula (1) usually starts with aminophenol derivatives in which the amino group suspected of doing harm to the reaction is protected with a suitable protective group and comprises the steps of alkylating the starting material on the oxygen atom in the presence of a base and thereafter removing the protective group. For instance, as exemplified by Reaction Scheme (I) given below, phenol (5) having the amino group protected as a carbamate group is alkylated and the ester is then hydrolyzed under basic conditions to produce an aniline derivative (see, for example, Reference Examples in Japanese Patent Public Disclosure Nos. Hei. 4-145071 and Hei. 4-164067) (see under Reference Examples 1 and 2 to be described later in this specification):

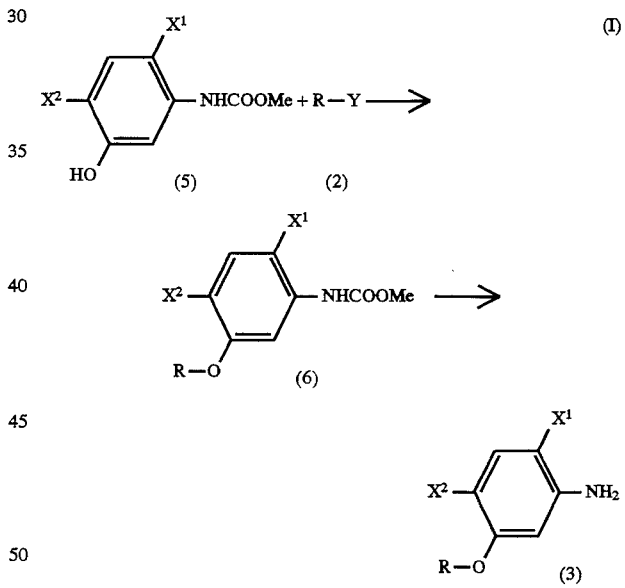

The production of aniline derivatives of the general formula (3) from bis(amino-substituted phenyl)carbonate derivatives of the general formula (4) usually starts with aminophenol derivatives that are prepared by first protecting with a suitable protective group the amino group suspected of doing harm to the reaction and by then hydrolyzing only the carbonate bond without impairing the protective group and the production process comprises the steps of alkylating the starting material on the oxygen atom in the presence of a base and thereafter removing the protective group. For instance, as exemplified by Reaction Scheme (II) given below, bis(5-alkoxycarbonyl-amino-2-chloro-4-fluorophenyl)carbonate (8) having the amino group protected as an alkyl carbamate group is hydrolyzed selectively to a phenol derivative (9), then alkylated and, thereafter, the carbamate group is hydrolyzed under basic conditions to produce an aniline derivative (3) (see, for example, Japanese Patent Public Disclosure No. Hei 5-17411 or Hei. 5-43525):

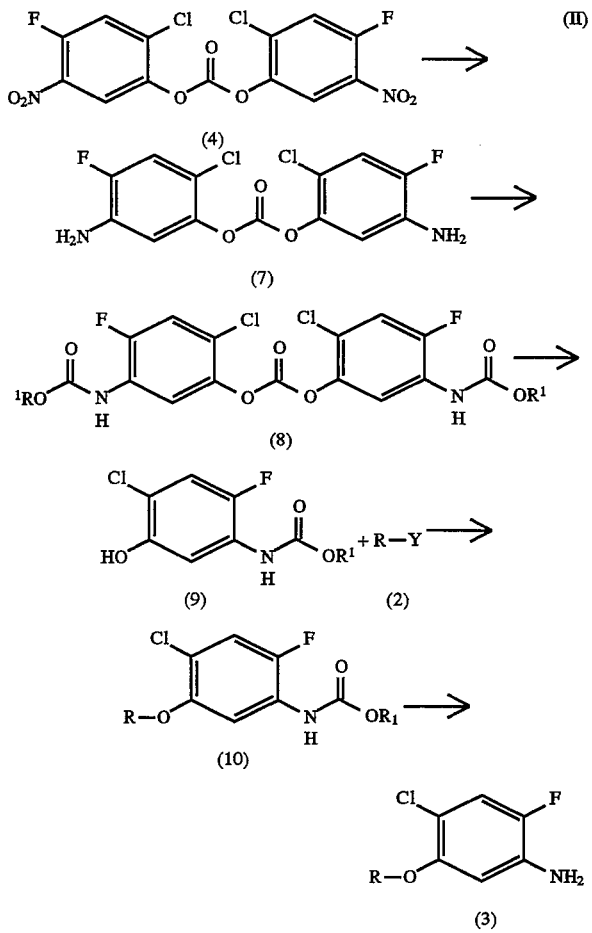

Thus, the prior art methods described above require additional steps for introducing and removing the amino protective group and this is disadvantageous from an economic viewpoint since not only is the reaction process extended but it is also necessary to use auxiliary materials as appropriate for the respective steps.

DISCLOSURE OF INVENTION

The present inventors conducted intensive studies to develop an industrially more advantageous process for producing aniline derivatives of the general formula (3) which can be used as starting materials for the manufacture of oxazolidinedione and tetrahydrophthalimide, as well as tetrahydroindazole derivatives which are useful as herbicidal active ingredients; as a result, it was revealed that the aniline derivatives of the general formula (3) could be produced in one step and in high yield by reacting the aminophenol derivatives of the general formula (1) or the bis(amino-substituted phenyl)carbonate derivatives of the general formula (4) with the alkylating agents of the general formula (2) in organic solvents under specified conditions without protecting the amino group in those derivatives. The present invention has thus been accomplished.

The aminophenol derivatives of the general formula (1) which are one class of the starting materials for use in the above-described production process are known compounds and may typically be produced by the process described in Japanese Patent Publication No. Hei. 2-26622. These aminophenol derivatives may be exemplified by 5-amino-2-chloro-4-fluorophenol, 5-amino-2-bromo-4-fluorophenyl, 5-amino-2,4-dichlorophenol, 5-amino-2,4-difluorophenol, etc. The other class of the starting materials, namely, the bis(amino-substituted phenyl)carbonate derivatives of the general formula (4) may typically be produced by the process described in Japanese Patent Public Disclosure No. Hei. 5-17411 or Hei. 5-43525. These carbonate derivatives may be exemplified by bis(5-amino-2-chloro-4-fluorophenyl)carbonate, bis(5-amino-2-bromo-4-fluorophenyl)carbonate, bis(5-amino-2,4-dichlorophenyl) carbonate, bis(5-amino-2,4-difluorophenyl)carbonate, etc.

The production processes of the present invention will now be described in greater detail.

When reacting the aminophenol derivatives of the general formula (1) or the bis(amino-substituted phenyl)carbonate derivatives of the general formula (4) with the alkylating agents of the general formula (2) in a two-layer system to produce the aniline derivatives of the general formula (3), the reaction is characterized by being performed in both an aqueous solution of an alkali metal hydroxide and an organic solvent in the presence of a phase transfer catalyst, and the alkali metal hydroxides may be exemplified by sodium hydroxide, potassium hydroxide, etc. The concentration of the alkali metal hydroxide in aqueous solution is not limited to any particular value but aqueous solutions of 24–48% sodium hydroxide which are readily available on an industrial scale may also be used in the reaction under consideration. From the viewpoint of yield, the aqueous solution of an alkali metal hydroxide is preferably used in an amount of at least one equivalent, more advantageously at least ten equivalents, in terms of the amount of the base, per equivalent of the reaction substrate.

The organic solvents to be used in the reaction may be of any types that will do no harm to the reaction and may be exemplified by tetrahydrofuran, diethyl ether, diisopropyl ether, benzene, toluene, xylene, chlorobenzene, hexane, etc. Among these, aromatic solvents such as toluene and chlorobenzene are particularly preferred from the viewpoint of yield.

The phase transfer catalyst may be selected from among quaternary ammonium salts, crown ethers, etc. and these may be exemplified by quaternary ammonium salts, such as tetramethylammonium chloride, tetramethylammonium bromide, tetraethylammonium chloride, tetraethylammonium bromide, tetrabutylammonium chloride, tetrabutylammonium bromide, trimethylbenzylammonium chloride, trimethylbenzylammonium bromide, triethylbenzylammonium chloride, triethylbenzylammonium bromide, cetyltrimethylammonium chloride, trioctylmethylbenzylammonium chloride, tetrabutylammonium hydrogen sulfide, tetraethylammonium p-toluenesulfonate, tetrapropylammonium hydroxide, trimethylbenzylammonium hydroxide, etc., and crown ethers such as 15-crown-5,18-crown-6, benzo-15-crown-5, dibenzo-18-crown-6, dicyclohexano-18-crown-6, etc.

The amount of use of the phase transfer catalyst is not limited to any particular value but a so-called "catalytic amount" will suffice and the end product can be obtained in high yield by using the phase transfer catalyst in an amount of $1/10,000$–$1/2$ equivalent, preferably $1/1,000$–$1/10$ equivalent, per equivalent of the substrate.

The bis(amino-substituted phenyl)carbonate derivatives of the general formula (4) can stoichiometrically react with two molecules of the alkylating agent (2) and, hence, from the viewpoint of yield, the alkylating agent (2) is preferably used in an amount of at least two equivalents per equivalent of the bis(amino-substituted phenyl)carbonate derivatives of the general formula (4).

The reaction may typically be carried out at 30°–120° C. but if it is performed under heating at 50°–100° C., the reaction can be completed within a shorter time to give the end product in a higher yield.

When reacting the aminophenol derivatives of the general formula (1) with the alkylating agents of the general formula (2) in an organic solvent in the presence of an alkali metal carbonate to produce the aniline derivatives of the general formula (3), the alkali metal carbonate may be exemplified by potassium carbonate, sodium carbonate, etc. These bases may be used as solids in the reaction or, alternatively, their aqueous or alcoholic solutions may be used. From the viewpoint of yield, these bases are preferably used in amounts of at least one equivalent per equivalent of the reaction substrate.

It is essential that the reaction under consideration be performed in an organic solvent. The organic solvent to be used may be of any types that will do no harm to the reaction and may be exemplified by acetonitrile, acetone, N,N-dimethylformamide, tetrahydrofuran, diethyl ether, diisopropyl ether, methanol, ethanol, benzene, toluene, xylene, chlorobenzene, hexane, octane, chloroform, dichloromethane, etc. The reaction may typically be carried out at room temperature to 120° C. but it can be completed within a shorter time by performance under heating.

The alkylating agent of the general formula (2) is used in either case of the production process. The cycloalkyl group represented by R in the general formula (2) may be exemplified by a cyclopropyl group, a cyclopentyl group, a cyclohexyl group, a cyclooctyl group, a cyclododecyl group, etc. These cycloalkyl groups may be replaced by alkyl groups of 1–4 carbon atoms, etc. The alkynyl group as R may be exemplified by a propargyl group, 1-butyn-3-yl group, 3-butyn-1-yl group, 2-butyn-1-yl group, 1-pentyn-2-yl group, 1-pentyn-3-yl group, 2-pentyn-1-yl group, 3-hexyn-1-yl group, 5-hexyn-1-yl group, etc.

The leaving group represented by Y may be exemplified by halogen atoms such as chlorine atom, bromine atom, iodine atom, etc., and sulfonyloxy groups such as p-toluenesulfonyloxy group, benzenesulfonyloxy group, methanesulfonyloxy group, trifluoromethanesulfonyloxy group, etc.

Hence, the alkylating agents of the general formula (2) may be exemplified by cyclopropyl bromide, cyclopentyl bromide, cyclopentyl iodide, cyclohexyl bromide, cyclooctyl bromide, cyclododecyl bromide, cyclopentyl p-toluenesulfonate, cyclopentyl benzenesulfonate, cyclopentyl methanesulfonate, cyclopentyl trifluoromethanesulfonate, (3-methylcyclopentyl) p-toluenesulfonate, (3-methylcyclopentyl) benzenesulfonate, (3-methylcyclopentyl)methanesulfonate, (2-methylcyclopentyl) p-toluenesulfonate, (2-methylcyclopentyl)benzenesulfonate, (2-methylcyclopentyl)methanesulfonate, cyclohexyl p-toluenesulfonate, cyclohexyl benzenesulfonate, cyclohexyl methanesulfonate, cyclooctyl p-toluenesulfonate, cyclooctyl methanesulfonate, cyclododecyl p-toluenesulfonate, cyclododecyl methanesulfonate, propargyl bromide, propargyl iodide, 3-bromo-1-butyne, 1-bromo-3-butyne, 1-bromo-2-butyne, 1-chloro-2-butyne, 1-bromo-3-pentyne, 1-bromo-5-hexyne, propargyl p-toluenesulfonate, propargyl benzenesulfonate, propargyl methanesulfonate, (1-butyn-3-yl) p-toluenesulfonate, (1-butyn-3-yl)benzenesulfonate, (1-butyn-3-yl) methanesulfonate, (2-butyn-1-yl) p-toluenesulfonate, (2-butyn-1-yl)methanesulfonate, (3-butyn-1-yl) p-toluenesulfonate, (3-butyn-1-yl)methanesulfonate, (3-pentyn-1-yl) p-toluenesulfonate, (3-pentyn-1-yl) methanesulfonate, (1-pentyn-3-yl) p-toluenesulfonate, (1-pentyn-3-yl)methanesulfonate, etc. Commercial grades of these compounds may be used as they are; sulfonates may be easily prepared by reacting the corresponding cycloalkyl alcohols and substituted sulfonyl chlorides in the presence of a base (see Reference Examples 3–9 to be given later in this specification). When using bromides or sulfonates as the alkylating agent, the reaction time can be shortened and the yield improved by performing the reaction in the presence of an iodide such as potassium iodide or sodium iodide.

In either case of the production process, the aniline derivative (3) can be obtained by effecting ordinary extracting procedures after the end of the reaction. If desired, conc. HCl may be added to a solution of the resulting aniline derivative (3), say, in toluene, whereby the aniline derivative (3) can be isolated as a hydrochloride salt; this hydrochloride salt may in turn be treated with a base, whereupon it can be readily reverted to the free aniline derivative (3).

The thus obtained aniline derivatives (3) may, in accordance with the Reaction Scheme (III) or (IV) set forth below, be converted to oxazolidinedione derivatives or tetrahydrophthalimide derivatives which are both useful as active ingredients of herbicides (see Reference Examples 10–13 to be given later in this specification).

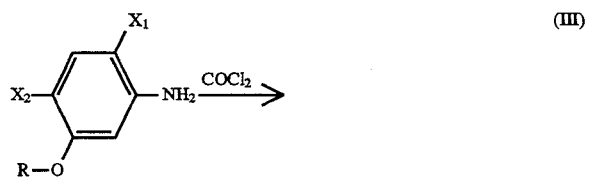

(III)

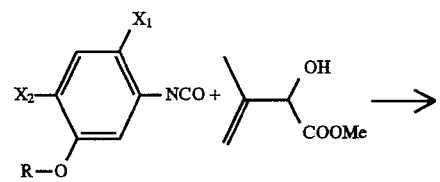

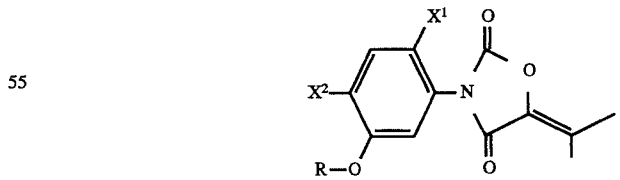

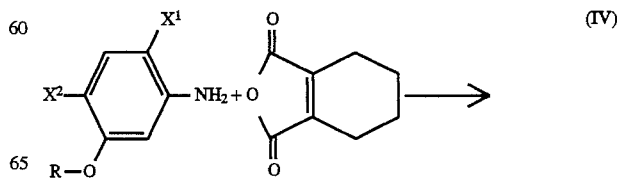

(IV)

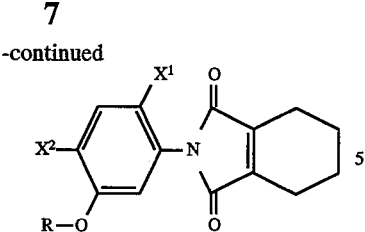

The following working examples and reference examples are provided for the purpose of further illustrating the present invention but are in no way to be taken as limiting.

EXAMPLE 1

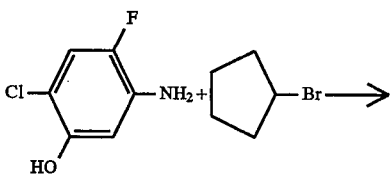

A two-necked, round-bottomed flask (25 cc) was charged with 5-amino-2-chloro-4-fluorophenol (1.015 g, 6.28 mmol), potassium carbonate (1.72 g, 12.4 mmol), potassium iodide (4.0 mg, 0.024 mmol) and solvent N,N-dimethylformamide (5 mL) and the mixture was stirred at 80° C. for 1 h. Subsequently, cyclopentyl bromide (1.00 g, 6.71 mmol) was added and the mixture was stirred at 80° C. for an additional 2 h. After the reaction was completed, the reaction mixture was cooled to room temperature and water (20 mL) was added, followed by extraction with toluene (20 mL×3). The organic layers were combined, washed with water (10 mL) and saturated brine (10 mL) and dried with anhydrous magnesium sulfate. After the desiccant was removed, the solvent was distilled off under vacuum to give 4-chloro-5-cyclopentyloxy-2-fluoroaniline (1.43 g, 6.23 mmol; yield=99.0%). BP: 143°–145° C./1.5 mmHg $^1$H-NMR(CDCl$_3$, TMS,ppm): δ1.40–2.00(8H,m), 3.72(2H, s), 4.67(1H,m), 6.39(1H,d,J$_{HF}$=9.0Hz), 7.04(1H,d,J$_{HF}$=11.0Hz). IR (neat, cm$^{-1}$): 3500, 3400, 1630, 1510, 1420, 1245, 1185.

EXAMPLE 2

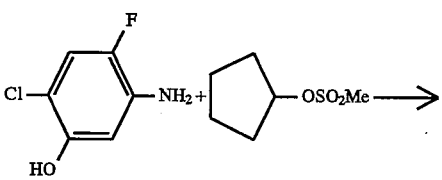

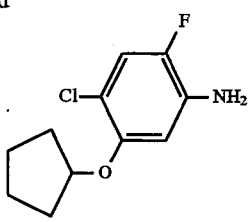

A three-necked flask (500 cc) equipped with a mechanical stirrer was charged with 5-amino-2-chloro-4-fluorophenol (10.0 g, 61.9 mmol), cyclopentyl methanesulfonate (10.3 g, 62.9 mmol) and tetrabutylammonium bromide (0.51 g, 1.58 mmol) to prepare a solution in toluene (50 mL). Subsequently, 48% sodium hydroxide in aqueous solution (30 mL) was added slowly and the mixture was stirred under heating at 80° C. for 2 h. After completion of the reaction, the reaction mixture was cooled to room temperature and water (150 mL) was added, followed by extraction with toluene (50 mL×2). The organic layers were combined, washed with water (100 mL×2) and placed under vacuum to distil off the solvent, thereby giving 4-chloro-5-cyclopentyloxy-2-fluoroaniline (13.5 g, 59.0 mmol; yield= 95.2%; purity on HPLC=98.6%).

EXAMPLE 3

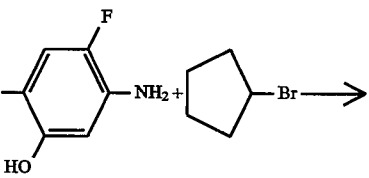

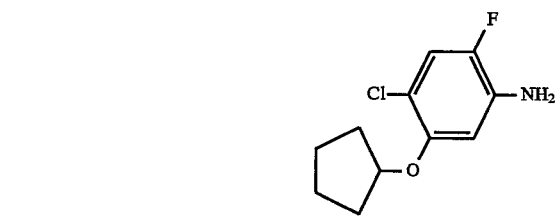

A round-bottomed flask (50 cc) equipped with a mechanical stirrer was charged with 5-amino-2-chloro-4-fluorophenol (1.03 g, 6.37 mmol), cyclopentyl bromide (1.32 g, 8.82 mmol), tetrabutylammonium bromide (152 mg, 0.47 mmol) and potassium iodide (300 mg, 1.81 mmol) to prepare a solution in toluene (5 mL). Subsequently, 40% sodium hydroxide in aqueous solution (5 mL) was added slowly and the mixture was stirred under heating at 80° C. for 4.5 h. After completion of the reaction, the reaction mixture was cooled to room temperature and water (10 mL) was added, followed by extraction with ethyl acetate (20 mL×3). The organic layers were combined, washed with water (10 mL) and saturated brine (10 mL) and dried with anhydrous magnesium sulfate. After the desiccant was removed, the solvent was distilled off under vacuum to give 4-chloro-5-cyclopentyloxy-2-fluoroaniline (1.45 g, 6.30 mmol; yield=99.0%).

EXAMPLE 4

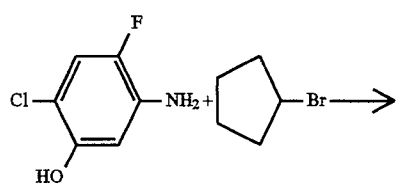

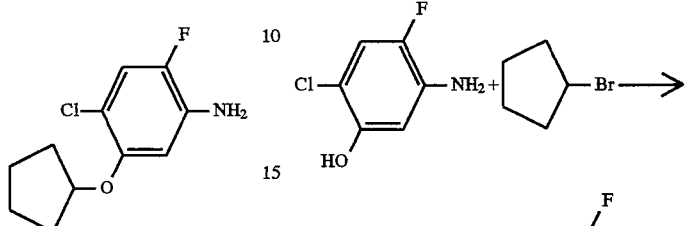

A three-necked flask (2,000 cc) equipped with a mechanical stirrer was charged with 5-amino-2-chloro-4-fluorophenol (75.0 g, 0.464 mol), cyclopentyl bromide (76.3 g, 0.512 mol), tetrabutylammonium bromide (3.03 g, 9.41 mmol) and potassium iodide (776 mg, 4.67 mmol) to prepare a solution in toluene (500 mL). Subsequently, 40% sodium hydroxide in aqueous solution (500 mL) was added slowly and the mixture was stirred under heating at 80° C. (in water bath at 85°–90° C.) for 7 h. After completion of the reaction, the reaction mixture was cooled to room temperature and water (500 mL) was added, followed by extraction with toluene (400 mL×2). The organic layers were combined, washed with water (100 mL) and saturated brine (100 mL) and dried with anhydrous magnesium sulfate. After the desiccant was removed, the solvent was distilled off under vacuum to give 4-chloro-5-cyclopentyloxy-2-fluoroaniline (87.2 g, 0.380 mol; yield=81.8%).

EXAMPLE 5

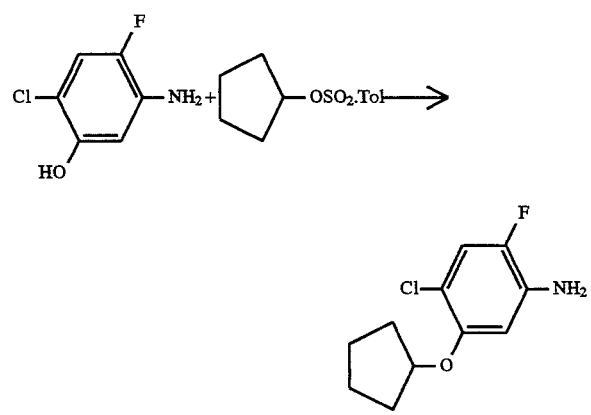

A round-bottomed flask (50 cc) equipped with a mechanical stirrer was charged with 5-amino-2-chloro-4-fluorophenol (1.02 g, 6.29 mmol), cyclopentyl p-toluenesulfonate (1.56 g, 6.50 mmol), tetrabutylammonium bromide (242 mg, 0.75 mmol) and potassium iodide (262 mg, 1.57 mmol) to prepare a solution in toluene (20 mL). Subsequently, 40% sodium hydroxide in aqueous solution (20 mL) was added slowly and the mixture was stirred under heating at 100° C. for 2 h. After completion of the reaction, the reaction mixture was cooled to room temperature and water (10 mL) was added, followed by extraction with ethyl acetate (20 mL×3). The organic layers were combined, washed with water (10 mL) and saturated brine (10 mL) and dried with anhydrous magnesium sulfate. After the desiccant was removed, the solvent was distilled off under vacuum to give 4-chloro-5-cyclopentyloxy-2-fluoroaniline (1.44 g, 6.27 mmol; yield=99.6%).

EXAMPLE 6

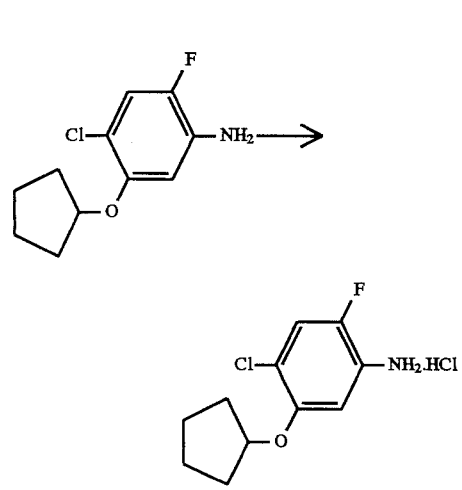

A three-necked flask (500 cc) equipped with a mechanical stirrer was charged with 5-amino-2-chloro-4-fluorophenol (400 g, 2.48 mol), potassium carbonate (857 g, 6.20 mol), potassium iodide (4.17 g, 25.1 mmol), N,N-dimethylformamide (750 mL) and water (112 mL), and the mixture was stirred at room temperature. Subsequently, cyclopentyl bromide (428 g, 2.73 mol) was added and the mixture was stirred at 80° C. for an additional 5 h. After completion of the reaction, the reaction mixture was cooled to room temperature and the solids were filtered off. Water (2,000 mL) was added to the filtrate and extraction was conducted with toluene (5,000 mL). Conc. HCl (300 mL) was added to the resulting toluene solution and the mixture was stirred thoroughly to precipitate 4-chloro-5-cyclopentyloxy-2-fluoroaniline hydrochloride salt. The white solids were isolated by filtration, washed successively with ethyl acetate and toluene, and dried (442.1 g, 1.66 mmol; yield=67.1%). MP: 145.0°–147° C. $^1$H-NMR (CDCl$_3$+DMSO-d$_6$,TMS,ppm): δ1.40–2.10 (8H,m), 4.74 (1H,m), 7.20(1H,d, J$_{HF}$=9.0Hz), 7.57(1H,d,J$_{HF}$=6.0Hz), 10.40(3H,brs). IR (KBr disk, cm$^{-1}$): 2850, 2610, 1500, 1200, 875.

EXAMPLE 7

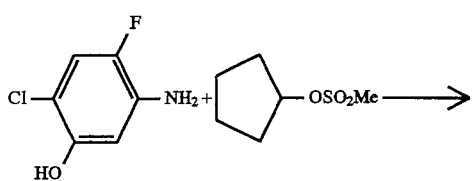

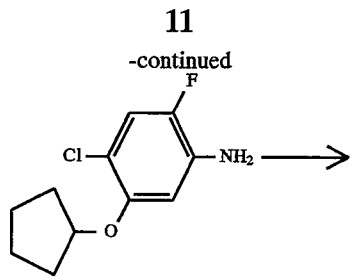

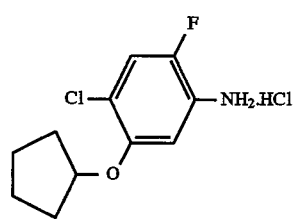

A round-bottomed flask (50 cc) was charged with 5-amino-2-chloro-4-fluorophenol (1.62 g, 10.0 mmol), cyclopentyl methanesulfonate (1.70 g, 10.4 mmol), tetrabutylammonium bromide (327 g, 1.01 mmol) and potassium iodide (333 mg, 2.00 mmol) to prepare a solution in toluene (10 mL). Subsequently, 48% sodium hydroxide in aqueous solution (7.5 mL) was added slowly and the mixture was stirred under heating at 80° C. for 1 h. After completion of the reaction, the reaction mixture was cooled to room temperature and water (10 mL) was added, followed by extraction with toluene (20 mL×2). The organic layers were combined and washed with water (10 mL) and saturated brine (10 mL). Conc. HCl (1.2 mL) was added to the resulting toluene solution and the mixture was stirred thoroughly to precipitate 4-chloro-5-cyclopentyloxy-2-fluoroaniline hydrochloride salt. The white solids were isolated by filtration, washed successively with ethyl acetate and toluene, and dried (2.33 g, 8.74 mmol; yield=87.4%).

EXAMPLE 8

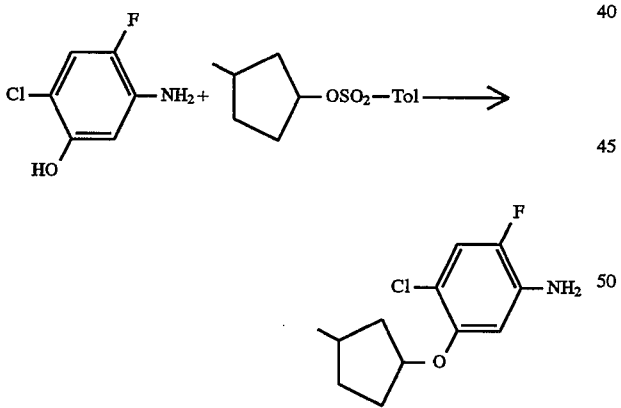

A round-bottomed flask (200 cc) equipped with a mechanical stirrer was charged with 5-amino-2-chloro-4-fluorophenol (3.00 g, 18.6 mmol), 3-methylcyclopentyl p-toluenesulfonate (4.60 g, 18.6 mmol), tetrabutylammonium bromide (300 mg, 0.93 mmol) and potassium iodide (300 mg, 1.81 mmol) to prepare a solution in toluene (30 mL). Subsequently, 48% sodium hydroxide in aqueous solution (30 mL) was added slowly and the mixture was stirred under heating at 100° C. for 48 h. After completion of the reaction, the reaction mixture was cooled to room temperature and water (50 mL) was added, followed by extraction with ethyl acetate (30 mL×3). The organic layers were combined, washed with water (10 mL) and saturated brine (10 mL) and dried with anhydrous magnesium sulfate. After the desiccant was removed, the solvent was distilled off under vacuum to give 2-fluoro-4-chloro-5-(3-methylcyclopentyloxy)aniline (1.94 g, 7.96 mmol; yield= 42.9%) as a brown oil. $^1$H-NMR(CDCl$_3$,TMS,ppm): δ1.02 and 1.10(total 3H, each d,J=6.0Hz), 1.22–2.58(7H,m), 3.75 (2H,brs), 4.65(1H,m), 6.33(1H,d,J$_{HF}$=8.0Hz), 6.98(1H,d, J$_{HF}$=10.0Hz)

EXAMPLE 9

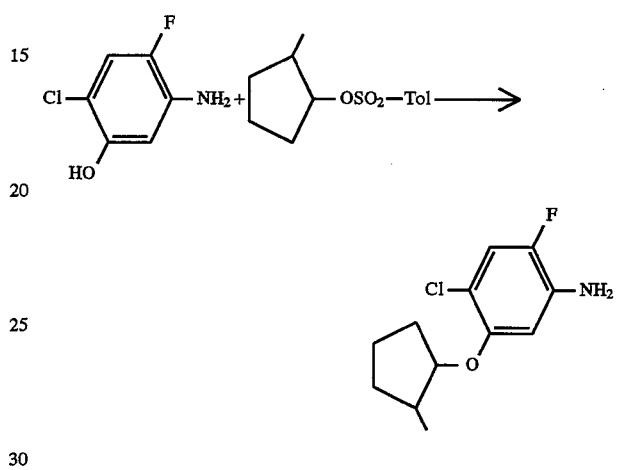

Reaction was conducted as in Example 8 except that the 3-methylcyclopentyl p-toluenesulfonate was replaced by 2-methylcyclopentyl p-toluenesulfonate, yielding 2-fluoro-4-chloro-5-(2-methylcyclopentyloxy)aniline as a brown oil. $^1$H-NMR(CDCl$_3$,TMS,ppm): δ1.04 and 1.15(total 3H, each d,J=7.3Hz), 1.40–2.40(7H,m), 3.66(2H,brs), 4.15 and 4.42 (total 1H, each m), 6.35(1H,d,J$_{HF}$=9.0Hz), 6.99(1H,d,J$_{HF}$= 11.5Hz). IR (neat, cm$^{-1}$): 3400, 2975, 1630, 1510, 1245, 1190.

EXAMPLE 10

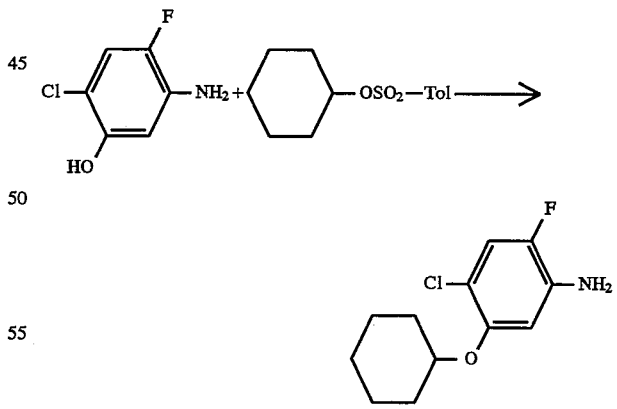

A round-bottomed flask (100 cc) equipped with a mechanical stirrer was charged with 5-amino-2-chloro-4-fluorophenol (1.03 g, 6.40 mmol), cyclohexyl p-toluenesulfonate (1.69 g, 6.66 mmol), tetrabutylammonium bromide (124 mg, 0.38 mmol) and potassium iodide (100 mg, 0.60 mmol) to prepare a solution in toluene (15 mL). Subsequently, 40% sodium hydroxide in aqueous solution (15 mL) was added slowly and the mixture was stirred under heating at 100° C. for 48 h. After completion of the reaction, the reaction mixture was cooled to room temperature and water (10 mL) was added, followed by extraction with ethyl acetate (20 mL×3). The organic layers were combined, washed with water (10 mL) and saturated brine (10 mL) and dried with anhydrous magnesium sulfate. After the desiccant was removed, the solvent was distilled off under vacuum to give a crude product (1.06 g). The product was separated and purified by silica gel column chromatography (ethyl acetate/hexane=⅑) to give 2-fluoro-4-chloro-5-cyclohexyloxyaniline (0.75 g, 3.08 mmol; yield= 48.1%). $^1$H-NMR(CDCl$_3$,TMS,ppm): δ1.15–2.06(10H,m), 3.46(2H, brs), 3.95–4.25(1H,m), 6.39 (1H,d,J$_{HF}$=9.0HZ), 6.97(1H,d,J$_{HF}$=11.5HZ). IR (neat, cm$^{-1}$): 3500, 3400, 2940, 2860, 1630, 1505, 1240, 1190.

EXAMPLE 11

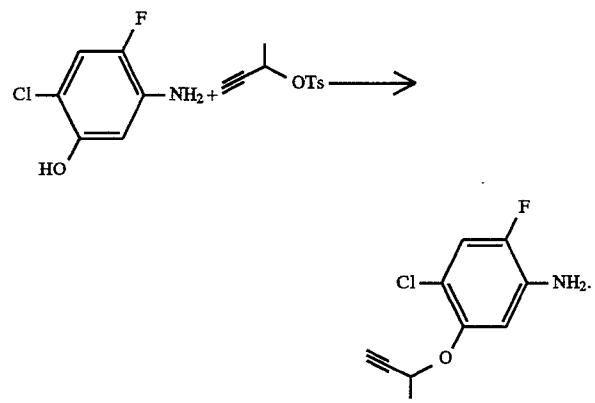

A round-bottomed flask (50 cc) was charged with 5-amino-2-chloro-4-fluorophenol (1.40 g, 8.67 mmol), (1-butyn-3-yl)tosylate (2.03 g, 9.00 mmol) and tetrabutylammonium bromide (71 mg, 0.22 mmol) to prepare a solution in toluene (25 mL). Subsequently, 48% sodium hydroxide in aqueous solution (6 mL) was added slowly and the mixture was stirred under heating at 60° C. for 2 h. After completion of the reaction, the reaction mixture was cooled to room temperature and water (15 mL) was added, followed by extraction with toluene (10 mL×2). The organic layers were combined and washed with water (10 mL×2). The solvent was distilled off under vacuum from the resulting toluene solution, thereby giving 4-chloro-2-fluoro-5-{(1-butyn-3-yl)oxy}aniline (1.04 g, 4.87 mmol; yield=56.1%). MP: 74.5°–75.5° C. $^1$H-NMR(CDCl$_3$,TMS,ppm): δ1.60 (3H,d,J=6.3Hz), 2.48(1H, d,J=1.5Hz), 3.46(2H,brs), 4.72 (1H,d&q,J=6.3 and 1.5Hz), 6.62(1H,d,J$_{HF}$=7.5Hz), 7.01 (1H, d,J$_{HF}$=10.0Hz).

EXAMPLE 12

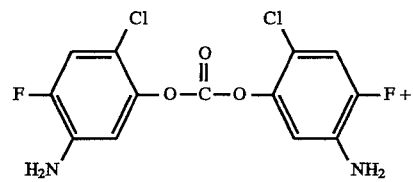

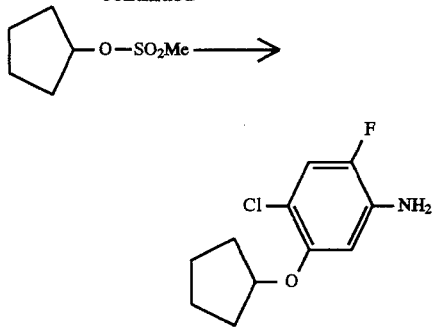

A round-bottomed flask (50 cc) was charged with bis(5-amino-2-chloro-4-fluorophenyl)carbonate (1.50 g, 4.29 mmol), cyclopentyl methanesulfonate (1.50 g, 9.15 mmol) and tetrabutylammonium bromide (70 mg, 0.22 mmol) to prepare a solution in toluene (12 mL). Subsequently, 48% sodium hydroxide in aqueous solution (6 mL) was added slowly and the mixture was stirred under heating at 80° C. for 3 h. After completion of the reaction, the reaction mixture was cooled to room temperate and water (15 mL) was added, followed by extraction with toluene (10 mL×2). The organic layers were combined and washed with water (10 mL×2). The solvent was distilled off under vacuum from the resulting toluene solution, thereby giving 4-chloro-5-cyclopentyloxy-2-fluoroaniline (1.94 g, 8.45 mmol; yield= 98.4%; purity on HPLC=94.3%). BP: 143°–145° C./1.5 mmHg $^1$H-NMR(CDCl$_3$,TMS,ppm): δ1.40–2.00(8H,m), 3.72(2H,s), 4.76(1H,m), 6.39(1H,d,J$_{HF}$=9.0Hz), 7.04(1H,d, J$_{HF}$=11.0Hz). IR (neat, cm$^{-1}$): 3500, 3400, 1630, 1510, 1420, 1245, 1185.

EXAMPLE 13

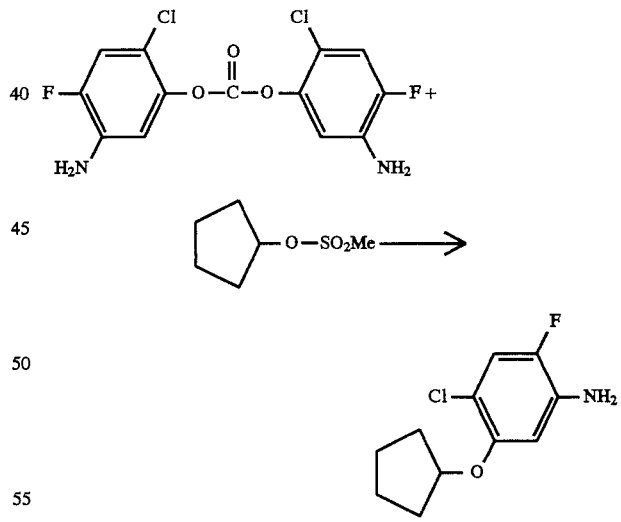

A round-bottomed flask (50 cc) was charged with bis(5-amino-2-chloro-4-fluorophenyl)carbonate (1.51 g, 4.34 mmol), cyclopentyl methanesulfonate (1.51 g, 9.21 mmol) and tetrabutylammonium bromide (70 mg, 0.22 mmol) to prepare a solution in toluene (8 mL). Subsequently, 48% sodium hydroxide in aqueous solution (4 mL) was added slowly and the mixture was stirred under heating at 80° C. for 1 h. Subsequently, 48% sodium hydroxide in aqueous solution (4 mL) was added slowly and the mixture was stirred under heating at 80° C. for an additional 1 h. After completion of the reaction, the reaction mixture was cooled to room temperature and water (15 mL) was added, followed by extraction with toluene (10 mL×2). The organic layers were combined and washed with water (10 mL×2). The solvent was distilled off under vacuum from the resulting toluene solution, thereby giving 4-chloro-5-cyclopentyloxy-2-fluoroaniline (1.92 g, 8.36 mmol; yield=96.4%; purity on HPLC=94.4%).

EXAMPLE 14

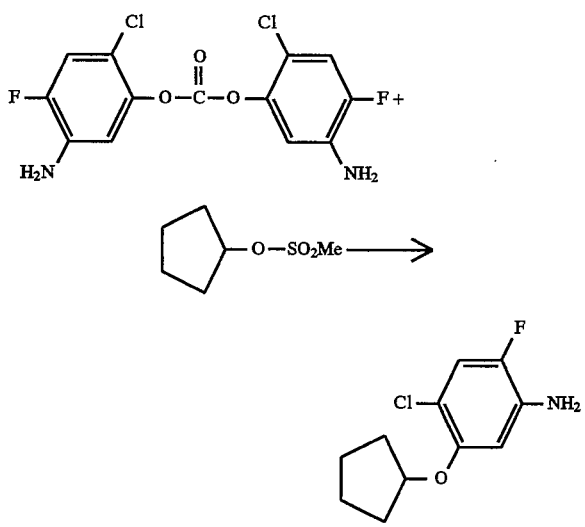

A round-bottomed flask (300 cc) was charged with bis(5-amino-2-chloro-4-fluorophenyl)carbonate (10.0 g, 28.6 mmol), cyclopentyl methanesulfonate (10.1 g, 61.3 mmol) and tetrabutylammonium bromide (463 mg, 1.43 mmol) to prepare a solution in toluene (55 mL). Subsequently, 48% sodium hydroxide in aqueous solution (28 mL) was added slowly and the mixture was stirred under heating at 80° C. for 30 min. Subsequently, 48% sodium hydroxide in aqueous solution (27 mL) was added slowly over 30 min and the mixture was stirred under heating at 80° C. for an additional 1.0 h. After completion of the reaction, the reaction mixture was cooled to room temperature and water (100 mL) was added, followed by extraction with toluene (50 mL×2). The organic layers were combined and washed with water (100 mL×2). The solvent was distilled off under vacuum from the resulting toluene solution, thereby giving 4-chloro-5-cyclopentyloxy-2-fluoroaniline (12.6 g, 54.7 mmol; yield=95.4%; purity on HPLC=83.8%).

EXAMPLE 15

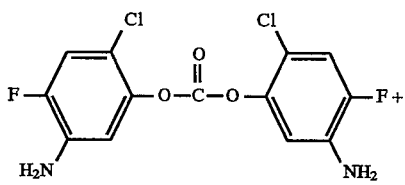

-continued

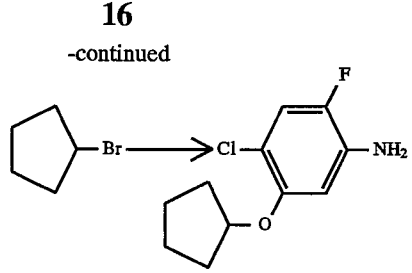

A round-bottomed flask (50 cc) was charged with bis(5-amino-2-chloro-4-fluorophenyl)carbonate (1.52 g, 4.36 mmol), cyclopentyl bromide (1.39 g, 9.29 mmol) and tetrabutylammonium bromide (74 mg, 0.23 mmol) to prepare a solution in toluene (12 mL). Subsequently, 48% sodium hydroxide in aqueous solution (6 mL) was added slowly and the mixture was stirred under heating at 80° C. for 1 h. After completion of the reaction, the reaction mixture was cooled to room temperature and water (15 mL) was added, followed by extraction with toluene (10 mL×2). The organic layers were combined and washed with water (10 mL×2). The solvent was distilled off under vacuum from the resulting toluene solution, thereby giving 4-chloro-5-cyclopentyloxy-2-fluoroaniline (1.93 g, 8.40 mmol; yield=96.3% ).

EXAMPLE 16

A round-bottomed flask (50 cc) was charged with bis(5-amino-2-chloro-4-fluorophenyl)carbonate (1.53 g, 4.39 mmol), propargyl bromide (1.11 g, 9.36 mmol) and tetrabutylammonium bromide (70 mg, 0.22 mmol) to prepare a solution in toluene (10 mL). Subsequently, 48% sodium hydroxide in aqueous solution (5 mL) was added slowly and the mixture was stirred under heating at 80° C. for 1 h. After completion of the reaction, the reaction mixture was cooled to room temperature and water (15 mL) was added, followed by extraction with toluene (10 mL×2). The organic layers were combined and washed with water (10 mL×2). The solvent was distilled off under vacuum from the resulting toluene solution, thereby giving 4-chloro-2-fluoro-5-propargyloxyaniline (1.61 g, 8.08 mmol; yield=92.0%).
$^{1}$H-NMR(CDCl$_{3}$,TMS,ppm): δ2.54(1H,t,J=2.3Hz), 3.79 (2H,brs), 4.70(2H,d,J=2.3Hz), 6.58(1H,d,J$_{HF}$=8.9Hz), 7.07 (1H,d,J$_{HF}$=11.2Hz).

EXAMPLE 17

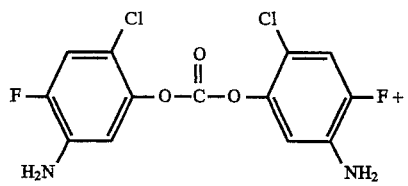

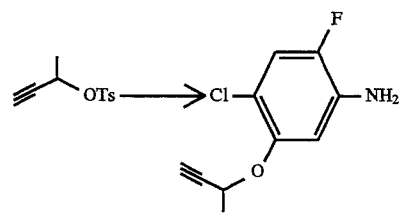

A round-bottomed flask (50 cc) was charged with bis(5-amino-2-chloro-4-fluorophenyl)carbonate (1.50 g, 4.30 mmol), (1-butyn-3-yl)tosylate (2.03 g, 9.02 mmol) and tetrabutylammonium bromide (71 mg, 0.22 mmol) to prepare a solution in toluene (25 mL). Subsequently, 48% sodium hydroxide in aqueous solution (6 mL) was added slowly and the mixture was stirred under heating at 60° C. for 2 h. After completion of the reaction, the reaction mixture was cooled to room temperature and water (15 mL) was added, followed by extraction with toluene (10 mL×2). The organic layers were combined and washed with water (10 mL×2). The solvent was distilled off under vacuum from the resulting toluene solution, thereby giving 4-chloro-2-fluoro-5-{(1-butyn-3-yl)oxy}aniline (1.12 g, 5.24 mmol; yield=61.0%).

REFERENCE EXAMPLE 1

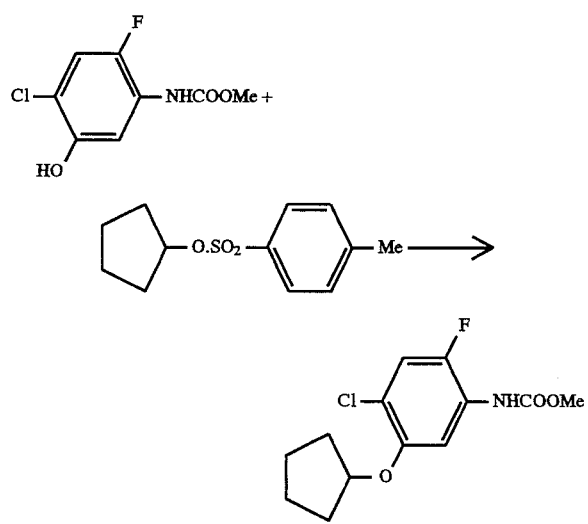

A 10-L three-necked flask equipped with a mechanical stirrer and a Dimroth condenser was charged with methyl N-(4-chloro-2-fluoro-5-hydroxyphenyl)carbamate (1.64 kg, 7.47 mol), cyclopentyl p-toluenesulfonate (1.80 kg, 7.48 mol), potassium carbonate (1.03 kg, 7.46 mol) and potassium iodide (12.3 g, 1.0 mol %), followed by the addition of solvent acetone (7,500 mL). The mixture was heated under reflux for 4 h. After completion of the reaction, the reaction mixture was recovered and 0.5N HCl (20 L) was added with vigorous stirring. The precipitating methyl N-(4-chloro-5-cyclopentyloxy-2-fluorophenyl)carbamate as white solids (2.00 kg, 6.95 mol; yield=93.1%) was isolated by filtration and dried thoroughly. MP: 120.0°–123.0° C. $^1$H-NMR (CDCl$_3$,TMS,ppm): δ1.40–2.10(8H,m), 3.77(3H,s), 4.77 (1H,m), 6.82(1H,brs), 7.07(1H,d,J$_{HF}$=10.5Hz), 7.83(1H,d, J$_{HF}$=7.5Hz). IR (KBr disk, cm$^{-1}$): 1714, 1535, 1500, 1415, 1255, 1190.

REFERENCE EXAMPLE 2

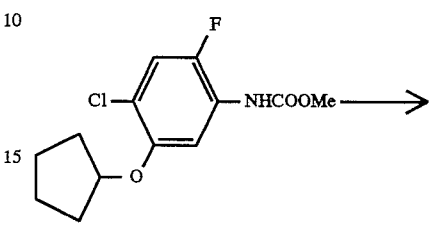

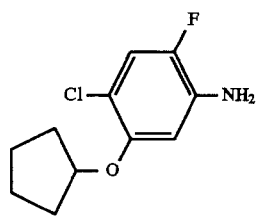

A 10-L three-necked flask equipped with a mechanical stirrer and a Dimroth condenser was charged with a solution of methyl N-(4-chloro-5-cyclopentyloxy-2-fluorophenyl) carbamate (2.25 kg, 7.85 mol) in ethanol (3,000 mL), followed by the addition of 4N potassium hydroxide in aqueous solution (4,750 mL); the mixture was heated under reflux for 5 h. After completion of the reaction, the reaction mixture was cooled to room temperature and water (5,000 mL) was added, followed by extraction with toluene (5,000 mL×2). The organic layers were washed and dried with anhydrous magnesium sulfate. The desiccant was separated by filtration and the solvent was distilled off under vacuum from the filtrate, thereby giving 4-chloro-5-cyclopentyloxy-2-fluoroaniline as an oil (1.75 kg, 7.62 mol; yield=98.3%).

REFERENCE EXAMPLE 3

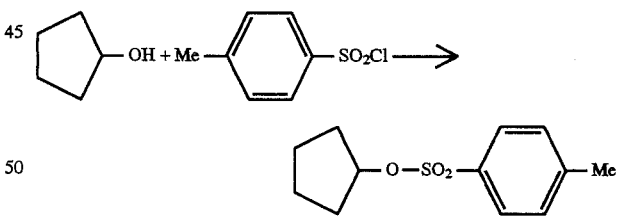

A round-bottomed separable flask (3,000 cc) equipped with a mechanical stirrer was charged with cyclopentyl alcohol (500 g, 5.80 mol) and p-toluenesulfonyl chloride (1,210 g, 6.35 mol), followed by the addition of pyridine (2,000 mL) under ice cooling to form a solution. The mixture was stirred for 8 h as it was warmed gradually to room temperature. After completion of the reaction, the reaction mixture was poured into ice water (3,000 mL) and stirred thoroughly. The precipitating solids were isolated by filtration, washed thoroughly with water and dried to give a white crystal of cyclopentyl p-toluenesulfonate (1,117 g; yield=80.1%). MP: <30° C. $^1$H-NMR(CDCl$_3$,TMS,ppm): δ1.23–2.07(8H,m), 2.45(3H,s), 4.98(1H,m), 7.38(2H,d,J= 9.0Hz), 7.85(2H,d,J=9.0Hz).

REFERENCE EXAMPLE 4

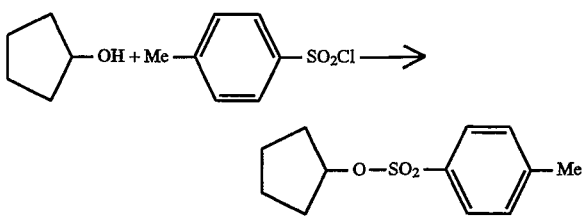

A round-bottomed flask (200 cc) was charged with cyclopentyl alcohol (10.0 g, 0.116 mol) and p-toluenesulfonyl chloride (24.3 g, 0.128 mol), followed by the addition of ether (100 mL) to form a solution. Subsequently, a powder of potassium hydroxide (32.5 g, 0.58 mol) was added slowly to the solution as it was cooled in a water bath at 10° C. or below. After the addition, the mixture was stirred at the same temperature for an additional 2 h. After completion of the reaction, the mixture was poured into ice water (20 mL), whereupon the organic layer separated from the aqueous layer. The organic layer was dried and concentrated under vacuum to give cyclopentyl p-toluenesulfonate as a pale yellow viscous liquid (22.0 g; yield=78.9%).

REFERENCE EXAMPLE 5

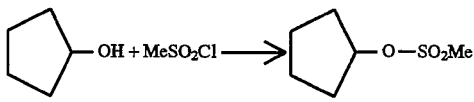

A round-bottomed flask (1,000 cc) equipped with a mechanical stirrer was charged with cyclopentyl alcohol (51.2 g, 0.595 mol) and methanesulfonyl chloride (75.1 g, 0.656 mol), followed by the addition of pyridine (200 mL) under ice cooling to form a solution. The solution was stirred for 6 h as it was warmed gradually to room temperature. After completion of the reaction, the reaction mixture was poured into ice water (300 mL) and extraction was conducted with ether (200 mL×3). The organic layers were washed with water, 1N HCl and saturated brine and dried with anhydrous magnesium sulfate. Distilling off the solvent under vacuum gave cyclopentyl methanesulfonate as a colorless oil (75.2 g, 0.458 mol; yield=77.0%). $^1$H-NMR (CDCl$_3$,TMS,ppm): δ1.54–2.03(8H,m), 3.01(3H,s), 5.19 (1H,m).

REFERENCE EXAMPLE 6

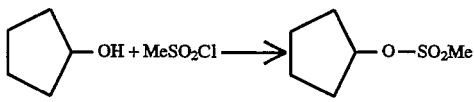

A round-bottomed flask (5,000 cc) equipped with a mechanical stirrer was charged with cyclopentyl alcohol (250 g, 2.90 mol) and methanesulfonyl chloride (350 g, 3.06 mol) followed by the addition of toluene (400 mL). Subsequently, pyridine (480 mL) was added dropwise over 1 h under ice cooling. After the adding, the mixture was stirred at the same temperature for an additional 3 h. After completion of the reaction, 2N HCl (1,500 mL) was added to the reaction mixture and the toluene layer was separated. The aqueous layer was subjected to extraction with toluene (500 mL) and the extract was combined with the toluene layer, followed by washing with 2N HCl (250 mL). The solvent was distilled off under vacuum from the resulting toluene solution, thereby giving cyclopentyl methanesulfonate as a colorless oil (433.4 g, 2.64 mol; yield=90.9%).

REFERENCE EXAMPLE 7

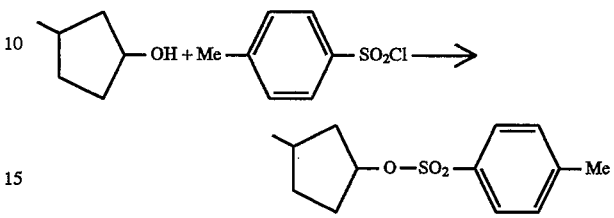

A round-bottomed flask (100 cc) was charged with 3-methylcyclopentyl alcohol (5.0 g, 49.9 mmol) and p-toluenesulfonyl chloride (10.0 g, 52.5 mmol), followed by the addition of pyridine (50 mL) under ice cooling to form a solution. The solution was stirred for 8 h as it was warmed gradually to room temperature. After completion of the reaction, the reaction mixture was poured into ice water and stirred thoroughly. After extraction with ether (100 mL×2), the organic layers were washed with 2N HCl, water and saturated brine, and dried with anhydrous magnesium sulfate. After the desiccant was removed, the solvent was distilled off under vacuum to give 3-methylcyclopentyl p-toluenesulfonate as a colorless clear oil (11.7 g; yield= 92.5%). MP: <30° C. $^1$H-NMR(CDCl$_3$,TMS,ppm): δ0.93 and 1.00(total 3H, each d,J=6.0Hz), 1.20–2.30(7H,m), 2.48 (3H,s), 4.97(1H,m), 7.38(2H,d,J=8.0Hz), 7.85(2H,d,J= 8.0Hz).

REFERENCE EXAMPLE 8

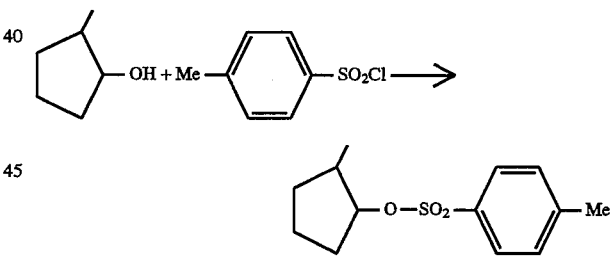

A three-necked flask (500 cc) equipped with a mechanical stirrer was charged with 2-methylcyclopentyl alcohol (21.19, 0.210 mol) and p-toluenesulfonyl chloride (48.3 g, 0.252 mol), followed by the addition of pyridine (170 ml) under ice cooling to form a solution. The solution was stirred for 10 h as it was warmed gradually to room temperature. After completion of the reaction, the reaction mixture was poured into ice water and stirred thoroughly. Following extraction with ether (200 mL×3), the organic layers were washed with 2N HCl, water and saturated brine and dried with anhydrous magnesium sulfate. After the desiccant was removed, the solvent was distilled off under vacuum to give 2-methylcyclopentyl p-toluenesulfonate as a colorless clear oil (49.7 9; yield=92.8%). $^1$H-NMR(CDCl$_3$,TMS,ppm): δ0.85(3H,d,J=7.5Hz), 1.41–2.10(TH,m), 2.43(3H,s), 4.42 and 4.80(total 1H, each m), 7.33(2H,d,J=9.0Hz), 7.80(2H, d,J=9.0Hz).

REFERENCE EXAMPLE 9

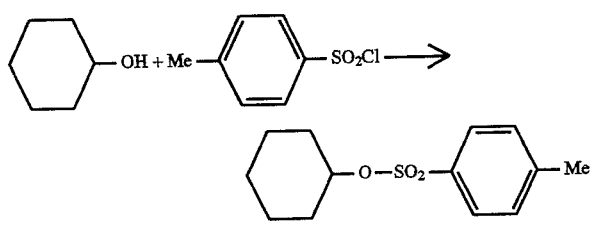

A round-bottomed flask (100 cc) was charged with cyclohexyl alcohol (5.01 9, 50.0 mmol) and p-toluenesulfonyl chloride (10.6 g, 55.6 mmol), followed by the addition of pyridine (20 mL) under ice cooling to form a solution. The solution was stirred for 8 h as it was warmed gradually to room temperature. After completion of the reaction, the reaction mixture was poured into ice water and stirred thoroughly. Following extraction with ether (50 mL×2), the organic layers were washed with 2N HCl, water and saturated brine and dried with anhydrous magnesium sulfate. After the desiccant was removed, the solvent was distilled off under vacuum to give cyclohexyl p-toluenesulfonate as a colorless clear oil (12.7 g; yield=99.0%). $^1$H-NMR(CDCl$_3$, TMS,ppm): δ1.12–1.88(10H,m), 2.43(3H,s), 4.46(1H,m), 7.28(2H,d,J=8.9Hz), 7.76(2H,d,J=8.9Hz).

REFERENCE EXAMPLE 10

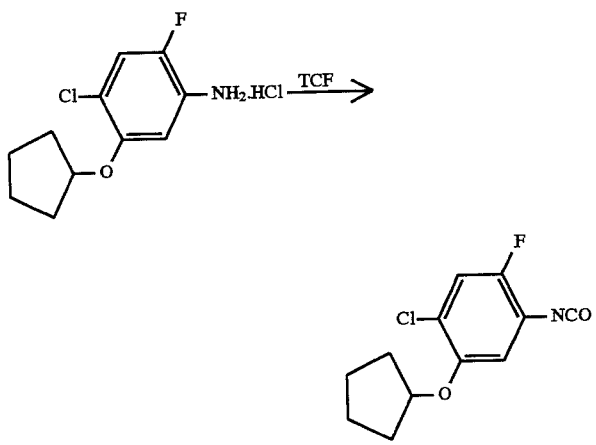

A flask (3,000 cc) equipped with a mechanical stirrer, a dropping funnel and a Dean-Stark tube was charged with 4-chloro-5-cyclopentyloxy-2-fluoroaniline hydrochloride salt (665 g, 2.50 mol) and toluene (1,500 mL) and the mixture was heated under reflux over an oil bath (120°–130° C.), with the effluent water (ca. 3 mL) being removed. Subsequently, the resulting toluene suspension was cooled (on an oil bath at 50° C.) and trichloromethyl chloroformate (TCF; 320 mL) was added dropwise at a rate that would cause no gas evolution. After the addition, the mixture was warmed gradually (15°–20° C./h). As soon as the warming started, gases began to evolve and the mixture became gradually homogeneous to form a completely uniform solution at 100°–110° C. Finally, the oil bath temperature was raised to the toluene reflux temperature and, with part of the toluene being distilled off, heating was continued (for ca. 4 h) until no more gases evolved. After completion of the reaction, the reaction solution was left to cool and the toluene was distilled off under vacuum to give 4-chloro-5-cyclopentyloxy-2-fluorophenylisocyanate as a brown oil (543 g, 2.12 mol; yield=84.8%). $^1$H-NMR(CDCl$_3$,TMS, ppm): δ1.50–2.10(8H,m), 4.67(1H,m), 6.60(1H,d,J$_{HF}$=7.5Hz), 7.12(1H,d,J$_{HF}$=10.5Hz). IR (neat, cm$^{-1}$) 2275, 1720, 1615, 1525, 1470, 1195.

REFERENCE EXAMPLE 11

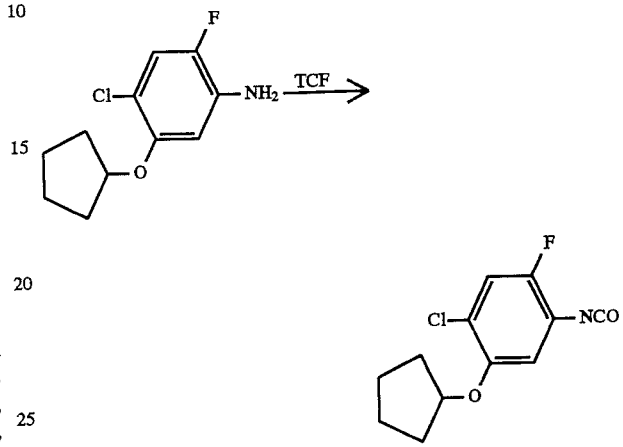

A solution of trichloromethyl chloroformate (TCF; 15 ml, 0.123 mol) in toluene (50 mL) was cooled in an ice water bath and to the cooled solution, a solution of 4-chloro-5-cyclopentyloxy-2-fluoroaniline (23.0 g, 0.10 mol) and triethylamine (0.5 mL) in toluene (50 mL) was added dropwise with thorough stirring. In the course of the adding, an ammonium salt precipitated and the solution turned to suspension, which was kept stirred for 1 h. Subsequently, the suspension was heated to 100° and stirred for another 1 h. After completion of the reaction, the toluene was distilled off under vacuum, whereby the desired 4-chloro-5-cyclopentyloxy-2-fluorophenylisocyanate could be obtained almost quantitatively as a reddish brown oil.

REFERENCE EXAMPLE 12

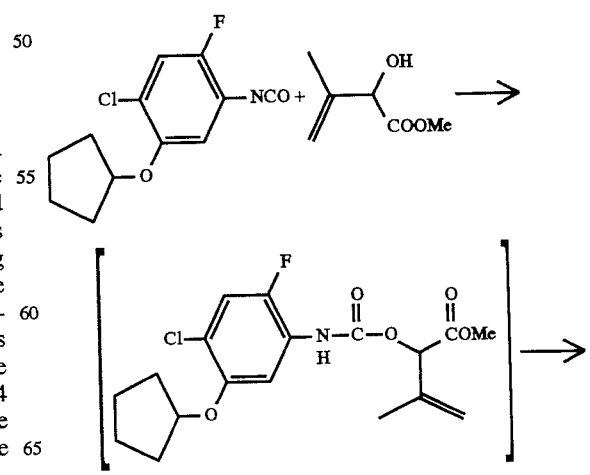

-continued

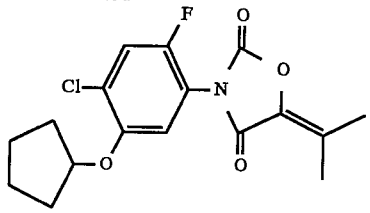

A 20-L stainless steel vessel equipped with a mechanical stirrer and a dropping funnel was charged with a solution of 4-chloro-5-cyclopentyloxy-2-fluorophenylisocyanate (4.00 kg, 15.6 mol) and methyl 2-hydroxy-3-methyl-3-butenoate (2.40 kg; purity=ca. 90%; 18.4 mol) in toluene (10 L). To the solution being cooled in an ice water bath, triethylamine (40 mL) was added dropwise slowly enough to ensure against the increase in the temperature of the solution. The solution was stirred at the same temperature for 3 h until TLC confirmed that the starting materials had disappeared. Subsequently, potassium carbonate (200 g) was added and, with the resulting methanol being removed with a fitted distillator, the mixture was stirred under heating in a water bath (100° C.) for 5 h. After completion of the reaction, the reaction mixture was washed with 1N HCl (10 L), 1N sodium hydroxide (10 L) and again with 1N HCl (10 L). The toluene layer was dried with anhydrous magnesium sulfate and the solvent was distilled off under vacuum; thereafter, hexane was added in an amount about one half of the resulting oil and the mixture was left to stand at room temperature, thereby producing 3N-(4-chloro-5-cyclopentyloxy-2-fluorophenyl)-5-isopropyliden-2,4-oxazolidinedione as whitish yellow solids (4.19 kg, 11.8 mol; yield=75.7%; primary crystal). MP: 104.5°–105.0° C. $^1$H-NMR(CDCl$_3$,TMS,ppm): δ1.49–1.97(8H,m), 2.03(3H, s), 2.31(3H,s), 4.73(1H,m), 6.88(1H,d,J$_{HF}$=6.6Hz), 7.33 (1H,d,J$_{HF}$=8.5Hz). IR (KBr disk, cm$^{-1}$): 2970, 1815, 1740, 1500, 1200.

REFERENCE EXAMPLE 13

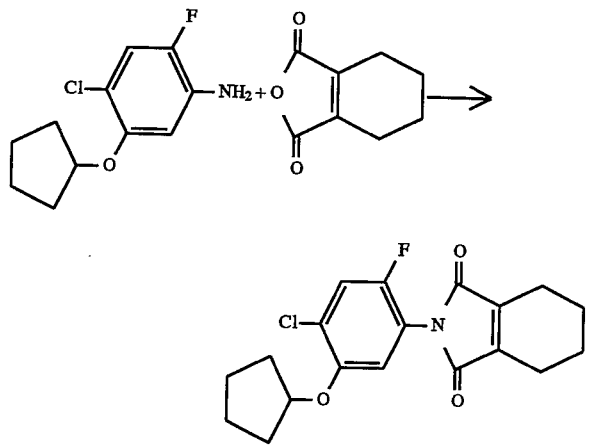

A solution of 4-chloro-5-cyclopentyloxy-2-fluoroaniline (0.50 g, 2.18 mmol) and 3,4,5,6-tetrahydrophthalic anhydride (0.398 g, 2.61 mmol) in acetic acids solution (3.0 mL) was stirred under reflux for 3 h. After completion of the reaction, water (20 mL) was added to the resulting reaction mixture and extraction was conducted with ethyl acetate (20 mL×3). The organic layers were dried with anhydrous magnesium sulfate and the solvent was distilled off under vacuum. The resulting pale yellow oil was separated and purified by silica gel column chromatography (ethyl acetate/ hexane=⅛), giving N-(4-chloro-5-cyclopentyloxy-2-fluorophenyl)-3,4,5,6-tetrahydrophthalimide as a colorless clear oil (0.513 g, 1.41 mmol; yield=65%). This could be obtained as white solids upon addition of ethanol and subsequent recrystallization. MP: 69.0°–75.2° C. $^1$H-NMR (CDCl$_3$,TMS,ppm): δ1.32–2.10(12H,m), 2.40(4H,m), 4.68 (1H,m), 6.75(1H,d,J$_{HF}$=7.0Hz), 7.20(1H, d,J$_{HF}$=9.0Hz). IR (neat, cm$^{-1}$): 1725, 1505, 1430, 1385, 1200.

We claim:

1. A process for producing an aniline derivative of the general formula (3):

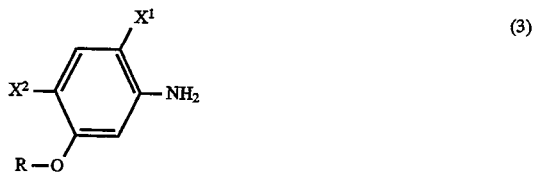

(where X$^1$ and X$^2$ represent a halogen atom and R represents an optionally substituted cycloalkyl group having 3–12 carbon atoms or an optionally substituted alkynyl group having 3–6 carbon atoms) by reacting a bis(amino-substituted phenyl)carbonate derivative of the general formula (4):

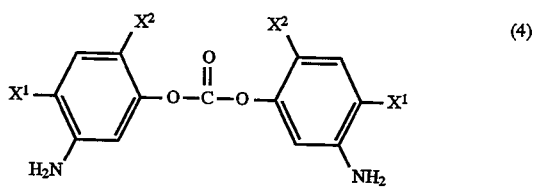

(where X$^1$ and X$^2$ represent a halogen atom) with an alkylating agent of the general formula (2):

(where R represents an optionally substituted cycloalkyl group having 3–12 carbon atoms or an optionally substituted alkynyl group having 3–6 carbon atoms, and Y represents a leaving group) in a two-layer system consisting of an aqueous solution of an alkali metal hydroxide and an organic solvent in the presence of a phase transfer catalyst.

2. A process according to claim 1 wherein the phase transfer catalyst is a quaternary ammonium salt.

3. A process according to claim 1 wherein the alkali metal hydroxide is sodium hydroxide and wherein the aqueous solution thereof has a concentration of 24–48%.

* * * * *